United States Patent [19]

Crowley et al.

[11] Patent Number: 5,334,722
[45] Date of Patent: Aug. 2, 1994

[54] FUNGICIDES

[75] Inventors: Patrick J. Crowley, Crowthorne; Alasdair T. Glen, Macclesfield; Rosamund A. Spence, Warminster; Kevin R. Lawson, High Wycombe, all of England

[73] Assignee: Imperial Chemical Industries PLC, London, England

[21] Appl. No.: 864,991

[22] Filed: Apr. 7, 1992

Related U.S. Application Data

[63] Continuation of Ser. No. 736,171, Jul. 26, 1991, abandoned.

[30] Foreign Application Priority Data

Jul. 27, 1990 [GB] United Kingdom ............ 9016578

[51] Int. Cl.$^5$ .............. C07D 213/26; C07D 213/38; C07D 213/50; C07D 213/61
[52] U.S. Cl. .................................. 546/289; 546/292; 546/308; 546/309
[58] Field of Search ............ 514/352; 546/289, 292, 546/305, 308, 309

[56] References Cited

U.S. PATENT DOCUMENTS

| | | |
|---|---|---|
| 3,467,753 | 9/1969 | Foster et al. |
| 3,654,291 | 4/1972 | Witzel et al. |
| 3,721,676 | 3/1973 | Witzel et al. |
| 4,666,938 | 5/1987 | Takahashi et al. |
| 4,999,381 | 3/1991 | Crowley et al. |

OTHER PUBLICATIONS

Chem. Abs. 112(19) 179010j (printout) and abstract of Japan Pat #01 180 886, Jul. 18, 1989, Kimura et al.

*Primary Examiner*—C. Warren Ivy
*Assistant Examiner*—D. Margaret M. Mach
*Attorney, Agent, or Firm*—William E. Dickheiser

[57] ABSTRACT

Fungicidal compounds of formula (I):

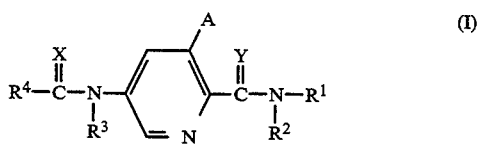

in which X and Y are independently O or S, and A and $R^1$ to $R^4$ have various specified values.

10 Claims, No Drawings

FUNGICIDES

This is a continuation of application Ser. No. 07/736,171, filed Jul. 26, 1991, now abandoned.

This invention relates to novel fungicidal acylaminopyridinecarboxamides, to processes for preparing them, to fungicidal compositions containing them and to methods of using them to combat fungi, especially fungal infections of plants.

According to the present invention there is provided a compound of the formula (I), A is fluoro, chloro, bromo, iodo, $C_{1-4}$ alkyl, $C_{1-4}$ alkoxy, halo($C_{1-4}$)alkyl, $C_{1-4}$ alkoxymethyl, $C_{1-4}$ alkylthiomethyl, $C_{2-4}$ alkenyl, $C_{2-4}$ alkynyl, $C_{1-4}$ alkoxycarbonyl, $C_{1-4}$ alkylcarbonyl, formyl, cyano, nitro or $C_{1-4}$ alkylthio; $R^1$ and $R^2$ are independently $C_{1-4}$ alkyl, $C_{3-6}$ alkenyl, (optionally substituted with halogen), $C_{3-6}$ alkynyl (optionally substituted with halogen), $C_{1-4}$ alkoxy, halo $C_{1-4}$ alkyl, $C_{3-6}$ cycloalkyl, $C_{3-6}$ cycloalkyl($C_{1-4}$)alkyl, $C_{1-4}$ alkoxy($C_{1-4}$)alkyl, $C_{1-4}$ alkylthio($C_{1-4}$)alkyl or cyano, or $R^1$ and $R^2$ together with the nitrogen to which they are attached join to form a morpholine, piperidine, pyrrolidine or azetidine ring, which may be optionally substitued with $C_{1-4}$ alkyl; $R^3$ is H or $R^3$ and $R^4$, together with the group C(O)N to which they are attached, join to form an azetidin-2-one ring which is optionally substituted with $C_{1-4}$ alkyl; $R^4$ is $C_{2-8}$ alkyl, $C_{2-8}$ alkenyl, $C_{2-8}$ alkynyl, or $C_{3-6}$ cycloalkyl, all of which may be optionally substituted with halogen, $C_{1-4}$ alkyl, $C_{1-4}$ alkoxy, $C_{1-4}$ alkylthio, cyano, $C_{1-4}$ alkylcarbonyl, $C_{1-4}$ alkoxycarbonyl, azido, nitro, isocyano or $NR^5R^6$ (where $R^5$ and $R^6$ are independently H, $C_{1-4}$ alkyl, $C_{1-4}$ alkylcarbonyl, or formyl); and X and Y are independently oxygen or sulphur.

Alkyl groups and the alkyl moiety of other alkyl-containing groups can be in the form of straight or branched chains. Examples are methyl, ethyl, propyl (n-and iso-propyl), butyl (n-, sec, iso- and t-butyl), 1,1-dimethylpropyl and 1,1-dimethylbutyl. Alkenyl and alkynyl groups can also be in the form of straight or branched chains. Examples are 1,1-dimethylbut-3-enyl and 1,1-dimethylprop-2-ynyl.

A preferred value of $R^4$ is $R(CH_3)_2C-$ in which R is a halogen (especially fluoro), $C_{1-4}$ alkyl (especially methyl or ethyl) or $C_{1-4}$ alkoxy (especially methoxy).

Halogen includes fluorine, chlorine and bromine.

In one aspect the invention provides a compound of formula (I) in which A is chloro, bromo, fluoro or $C_{1-4}$ alkyl; $R^1$ and $R^2$ are $C_{1-4}$ alkyl; $R^3$ is H; $R^4$ is $C_{2-8}$ alkyl optionally substituted with halogen or $C_{1-4}$alkoxy; and X and Y are both O.

The invention is illustrated by the compounds listed in Table I which follows. The compounds have the formula (II) in which the values of $R^1$, $R^2$, $R^4$ and A are given in the table.

TABLE I

| Compound No | $R^1$ | $R^2$ | $R^4$ | A | Mpt° C. |
|---|---|---|---|---|---|
| 1 | $CH_3$ | $CH_3$ | $(CH_3)_3C$ | Cl | |
| 2 | $CH_3$ | $CH_3$ | $(CH_3)_3C$ | Br | |
| 3 | $CH_3$ | $CH_3$ | $(CH_3)_3C$ | F | |
| 4 | $CH_3$ | $CH_3$ | $(CH_3)_3C$ | $CH_3$ | |
| 5 | $CH_3$ | $CH_3$ | $Br(CH_3)_2C$ | Cl | |
| 6 | $CH_3$ | $CH_3$ | $Cl(CH_3)_2C$ | Cl | |
| 7 | $CH_3$ | $CH_3$ | $F(CH_3)_2C$ | Cl | 159–162 |
| 8 | $CH_3$ | $CH_3$ | $CH_3CH_2(CH_3)_2C$ | Cl | |
| 9 | $CH_3$ | $CH_3$ | $F(CH_3)_2C$ | Br | 262 |
| 10 | $CH_3$ | $CH_3$ | $F(CH_3)_2C$ | F | |
| 11 | $CH_3$ | $CH_3$ | $F(CH_3)_2C$ | $CH_3$ | 140–145 |
| 12 | $CH_3$ | $CH_3$ | $CH_3CH_2(CH_3)_2C$ | Br | |
| 13 | $CH_3$ | $CH_3$ | $CH_3CH_2(CH_3)_2C$ | F | |
| 14 | $CH_3$ | $CH_3$ | $CH_3CH_2(CH_3)_2C$ | $CH_3$ | |
| 15 | $CH_3$ | $CH_3$ | $CH_3O(CH_3)_2C$ | Cl | |
| 16 | $CH_3$ | $CH_3$ | $CH_3O(CH_3)_2C$ | Br | |
| 17 | $CH_3$ | $CH_3$ | $CH_3O(CH_3)_2C$ | F | |
| 18 | $CH_3$ | $CH_3$ | $CH_3O(CH_3)_2C$ | $CH_3$ | |
| 19 | $CH_3$ | $CH_3CH_2$ | $(CH_3)_3C$ | Cl | |
| 20 | $CH_3$ | $CH_3CH_2$ | $(CH_3)_3C$ | Br | |
| 21 | $CH_3$ | $CH_3CH_2$ | $(CH_3)_3C$ | F | |
| 22 | $CH_3$ | $CH_3CH_2$ | $(CH_3)_3C$ | $CH_3$ | |
| 23 | $CH_3$ | $CH_3CH_2$ | $F(CH_3)_2C$ | Cl | |
| 24 | $CH_3$ | $CH_3CH_2$ | $F(CH_3)_2C$ | Br | gum+ |
| 25 | $CH_3$ | $CH_3CH_2$ | $F(CH_3)_2C$ | F | |
| 26 | $CH_3$ | $CH_3CH_2$ | $F(CH_3)_2C$ | $CH_3$ | |
| 27 | $CH_3$ | $(CH_3)_2CH$ | $F(CH_3)_2C$ | Cl | |
| 28 | $CH_3CH_2$ | $(CH_3)_2CH$ | $F(CH_3)_2C$ | Cl | |
| 29 | $CH_3CH_2$ | $CH_3CH_2$ | $F(CH_3)_2C$ | Cl | |
| 30 | $CH_3$ | $CH_2=CHCH_2$ | $F(CH_3)_2C$ | Cl | |
| 31 | $CH_3$ | $CH\equiv CCH_2$ | $F(CH_3)_2C$ | Cl | |
| 32 | $CH_3$ | * | $F(CH_3)_2C$ | Cl | |
| 33 | $CH_3$ | * | $F(CH_3)_2C$ | Cl | |
| 34 | —$CH_2CH_2CH_2$— | | $F(CH_3)_2C$ | Cl | |
| 35 | $CH_3$ | $CH_3$ | $CH_2=CHCH_2(CH_3)_2C$ | Cl | |
| 36 | $CH_3$ | $CH_3$ | $CH\equiv CCH_2(CH_3)_2C$ | Cl | |
| 37 | $CH_3$ | $CH_3$ | $F(CH_3)(CH_3CH_2)C$ | Cl | |
| 38 | $CH_3$ | $CH_3$ | $F(CH_3)((CH_3)_2CH)C$ | Cl | |
| 39 | $CH_3$ | $CH_3$ | $F(CH_3CH_2)_2C$ | Cl | |
| 40 | $CH_3$ | $CH_3$ | $F(CF_3)_2C$ | Cl | |
| 41 | $CH_3$ | $CH_3$ | $F(CF_3)(FCH_2)C$ | Cl | |
| 42 | $CH_3$ | $CH_3$ | $F(CH_3)_2C$ | I | |
| 43 | $CH_3$ | $CH_3$ | $F(CH_3)_2C$ | $CH_3O$ | |
| 44 | $CH_3$ | $CH_3$ | $F(CH_3)_2C$ | $CF_3$ | |
| 45 | $CH_3$ | $CH_3$ | $F(CH_3)_2C$ | $CH_2=CH$ | |

TABLE I-continued

| Compound No | R$^1$ | R$^2$ | R$^4$ | A | Mpt° C. |
|---|---|---|---|---|---|
| 46 | CH$_3$ | CH$_3$ | F(CH$_3$)$_2$C | CH≡C | |
| 47 | CH$_3$ | CH$_3$ | F(CH$_3$)$_2$C | CH$_3$S | |
| 48 | CH$_3$ | CH$_3$ | F(CH$_3$)$_2$C | CH$_3$CH$_2$ | |
| 49 | CH$_3$ | CH$_3$ | F(CH$_3$)$_2$C | CH$_3$OCH$_2$ | |
| 50 | CH$_3$ | FCH$_2$CH$_2$ | F(CH$_3$)$_2$C | Cl | |

*See Chemical Formulae later for these values of R$^2$.
+ $^1$H NMR data for compound No. 24: (270 MHz, CDCl$_3$) & 1.13(1.5H, t), 1.27(1.5H, t), 1.67(6H, d), 2.81(1.5H, s), 3.11(1.5H, s), 3.13(1H, q), 3.62(1H, q), 8.51(1H, d), 8.45(1H, bd), 8.55(1H, d) ppm.

The compounds of the invention can be made by, for example, the methods illustrated in Scheme 1. Throughout the Scheme R$^1$, R$^2$, R$^4$ and A are as defined before, and B is a halogen.

In Scheme 1, compounds of formula (II) can be prepared by reacting compounds of formula (X) with an acid chloride R$^4$COCl in a suitable organic solvent such as methylene chloride or toluene in the presence of a base such as a tertiary amine (for example triethylamine) or an alkali metal carbonate or hydroxide (for example sodium bicarbonate or sodium hydroxide).

Compounds of formula (X) can be made by reduction of nitro compounds of formula (IX) using standard methods known in the literature such as iron powder in aqueous ethanol, or tin in hydrochloric acid.

Amides of formula (IX) can be made from compounds of formula (VII) by first converting a compound (VII) into an acid chloride of formula (VIII) by treatment with a standard reagent such as thionyl chloride or oxalyl chloride. The acid chloride (VIII) is then reacted with an amine R$^1$R$^2$NH in a suitable organic solvent (such as methylene chloride or toluene) or in water, in the presence of a base (such as triethylamine or sodium bicarbonate or excess amine R$^1$R$^2$NH).

Compounds of formula (VII) can be made from compounds of formula (VI) by reaction with an oxidant (such as sodium chlorite, in water containing hydrogen peroxide, with or without an organic cosolvent such as acetonitrile).

Compounds of formula (VI) can be made by oxidation of compounds of formula (V) with a reagent such as selenium dioxide in a suitable solvent such as dioxan.

Compounds of general formula (V) can be made by hydrolysis of compounds of general formula (IV) under acidic conditions (for example with aqueous sulphuric acid) or under basic conditions (for example with aqueous alkali metal hydroxide).

Compounds of general formula (IV) can be made by reaction of compounds of general formula (III) with the alkali metal salt of a dialkylmalonate of general formula CH$_2$(COOR$^7$)$_2$ where R$^7$ is C$_{1-4}$ alkyl (generated by reacting the dialkylmalonate with for example sodium hydride or potassium methoxide) in a suitable solvent such as DMF or THF.

Compounds of general formula (III) can be made by methods known in the literature.

The compounds of the invention may also be prepared using methods and techniques described in EP-A-0381330 and in UK Application No. 9016577.0 and applications claiming priority therefrom, the contents of which are incorporated herein by reference.

In a further aspect, the invention provides processes as herein described for preparing the compounds of the invention. It also provides intermediate chemicals of formulae (IV) to (X), particularly those in which A is halo or alkyl.

The compounds of the invention show fungicidal activity across a range of plant diseases. They are, however, particularly active against the class of pathogens known as the phycomycetes (equivalent to the oomycetes). These include species of Phytophthora, Plasmopara, Peronospora and Pseudoperonospora. Examples of pathogens which the invention compounds are particularly useful for controlling are: *Plasmopara viticola* on vines; other downy mildews such as *Bremia lactucae* on lettuce; Peronospora spp. on soybeans, tobacco, onions and other hosts; *Pseudoperonospora humuli* on hops and *Pseudoperonospora cubensis* on cucurbits; *Phytophthora infestans* on potatoes and tomatoes and other Phytophthora spp. on vegetables, strawberries, avocado, pepper, ornamentals, tobacco, cocoa and other hosts; and Pythium sp on rice, horticultural plants, vegetables and turf.

The invention therefore provides a method of combating fungi which comprises applying to a plant, to a seed of a plant or to the locus of the plant or seed a fungicidally effective amount of a compound as hereinbefore defined, or a composition containing the same.

The compounds may be used directly for agricultural purposes but are more conveniently formulated into compositions using a carrier or diluent. The invention thus provides fungicidal compositions comprising a compound as hereinbefore defined and an acceptable carrier or diluent therefor.

The compounds can be applied in a number of ways. For example, they can be applied, formulated or unformulated, directly to the foliage of a plant, to seeds or to other medium in which plants are growing or are to be planted, or they can be sprayed on, dusted on or applied as a cream or paste formulation, or they can be applied as a vapour or as slow release granules.

Application can be to any part of the plant including the foliage, stems, branches or roots, or to soil surrounding the roots, or to the seed before it is planted, or to the soil generally, to paddy water or to hydroponic culture systems. The invention compounds may also be injected into plants or sprayed onto vegetation using electrodynamic spraying techniques or other low volume methods.

The term "plant" as used herein includes seedlings, bushes and trees. Furthermore, the fungicidal method of the invention includes preventative, protectant, prophylactic and eradicant treatments.

The compounds are preferably used for agricultural and horticultural purposes in the form of a composition. The type of composition used in any instance will depend upon the particular purpose envisaged.

The compositions may be in the form of dustable powders or granules comprising the active ingredient (invention compound) and a solid diluent or carrier, for example, fillers such as kaolin, bentonite, kieselguhr, dolomite, calcium carbonate, talc, powdered magnesia, fuller's earth, gypsum, diatomaceous earth and china clay. Such granules can be preformed granules suitable for application to the soil without further treatment. These granules can be made either by impregnating pellets of filler with the active ingredient or by pelleting a mixture of the active ingredient and powdered filler. Compositions for dressing seed may include an agent (for example, a mineral oil) for assisting the adhesion of the composition to the seed; alternatively the active ingredient can be formulated for seed dressing purposes using an organic solvent (for example, N-methylpyrrolidone, propylene glycol or N,N-dimethylformamide). The compositions may also be in the form of wettable powders or water dispersible granules comprising wetting or dispersing agents to facilitate the dispersion in liquids. The powders and granules may also contain fillers and suspending agents.

Emulsifiable concentrates or emulsions may be prepared by dissolving the active ingredient in an organic solvent optionally containing a wetting or emulsifying agent and then adding the mixture to water which may also contain a wetting or emulsifying agent. Suitable organic solvents are aromatic solvents such as alkylbenzenes and alkylnaphthalenes, ketones such as cyclohexanone and methylcyclohexanone, chlorinated hydrocarbons such as chlorobenzene and trichlorethane, and alcohols such as benzyl alcohol, furfuryl alcohol, butanol and glycol ethers.

Suspension concentrates of largely insoluble solids may be prepared by ball or bead milling with a dispersing agent with a suspending agent included to stop the solid settling.

Compositions to be used as sprays may be in the form of aerosols wherein the formulation is held in a container under pressure of a propellant, e.g. fluorotrichloromethane or dichlorodifluoromethane.

The invention compounds can be mixed in the dry state with a pyrotechnic mixture to form a composition suitable for generating in enclosed spaces a smoke containing the compounds.

Alternatively, the compounds may be used in microencapsulated form. They may also be formulated in biodegradable polymeric formulations to obtain a slow, controlled release of the active substance.

By including suitable additives, for example additives for improving the distribution, adhesive power and resistance to rain on treated surfaces, the different compositions can be better adapted for various utilities. Other additives may be included to improve the biological efficacy of the various formulations. Such additives can be surface active materials to improve the wetting and retention on surfaces treated with the formulation and also the uptake and mobility of the active material, or additionally can include oil based spray additives. For example, certain mineral oil and natural plant oil (such as soya bean and rape seed oil) additives have been found to enhance several-fold foliar protectant activity against, for example, *Plasmopara viticola*.

The invention compounds can be used as mixtures with fertilisers (e.g. nitrogen-, potassium- or phosphorus-containing fertilisers). Compositions comprising only granules of fertiliser incorporating, for example coated with, the compound are preferred. Such granules suitably contain up to 25% by weight of the compound. The invention therefore also provides fertiliser composition comprising a fertiliser and the compound of general formula (I) or a salt or metal complex thereof.

Wettable powders, emulsifiable concentrates and suspension concentrates will normally contain surfactants, e.g. a wetting agent, dispersing agent, emulsifying agent or suspending agent. These agents can be cationic, anionic or non-ionic agents.

Suitable cationic agents are quaternary ammonium compounds, for example, cetyltrimethylammonium bromide. Suitable anionic agents are soaps, salts of aliphatic monoesters of sulphuric acid (for example, sodium lauryl sulphate), and salts of sulphonated aromatic compounds (for example, sodium dodecylbenzenesulphonate, sodium, calcium or ammonium lignosulphonate, butylnaphthalene sulphonate, and a mixture of sodium diisopropyl- and triisopropylnaphthalene sulphonates).

Suitable non-ionic agents are the condensation products of ethylene oxide with fatty alcohols such as oleyl or cetyl alcohol, or with alkyl phenols such as octyl- or nonylphenol and octylcresol. Other non-ionic agents are the partial esters derived from long chain fatty acids and hexitol anhydrides, the condensation products of the said partial esters with ethylene oxide, and the lecithins. Suitable suspending agents are hydrophilic colloids (for example, polyvinylpyrrolidone and sodium carboxymethylcellulose), and swelling clays such as bentonite or attapulgite.

Compositions for use as aqueous dispersions or emulsions are generally supplied in the form of a concentrate containing a high proportion of the active ingredient, the concentrate being diluted with water before use. These concentrates should preferably be able to withstand storage for prolonged periods and after such storage be capable of dilution with water in order to form aqueous preparations which remain homogeneous for a sufficient time to enable them to be applied by conventional spray equipment. The concentrates may conveniently contain up to 95%, suitably 10–85%, for example 25–60%, by weight of the active ingredient. After dilution to form aqueous preparations, such preparations may contain varying amounts of the active ingredient depending upon the intended purpose, but an aqueous preparation containing 0.0005% or 0.01% to 10% by weight of active ingredient may be used.

The compositions of this invention may contain other compounds having biological activity, e.g. compounds having similar or complementary fungicidal activity or which possess plant growth regulating, herbicidal or insecticidal activity.

A fungicidal compound which may be present in the composition of the invention may be one which is capable of combating ear diseases of cereals (e.g. wheat) such as Septoria, Gibberella and Helminthosporium spp., seed and soil-borne diseases and downy and powdery mildews on grapes and powdery mildew and scab on apple, etc. By including another fungicide, the composition can have a broader spectrum of activity than the compound of general formula (I) alone. Further the other fungicide can have a synergistic effect on the fungicidal activity of the compound of general formula (I). Examples of fungicidal compounds which may be included in the composition of the invention are (RS)-1-aminopropylphosphonic acid, (RS)-4-(4-chlorophenyl)-2-phenyl-2-(1H-1,2,4-triazol-1-ylmethyl)butyronitrile, (Z)-N-but-2-enyloxymethyl-2-chloro-2',6'-diethylacetanilide, 1-(2-cyano-2-methoxyiminoacetyl)-3-ethyl urea, 3-(2,4-dichlorophenyl)-2-(1H-1,2,4-triazol-1-yl)quinazolin-4(3H)-one, 4-bromo-2-cyano-N,N-dimethyl-6-trifluoromethylbenzimidazole-1-sulphonamide, 5-ethyl-5,8-dihydro-8-oxo(1,3)-dioxol(4,5-g)quinoline-7-carboxylic acid, α-[N-(3-chloro-2,6-xylyl)-2-methoxyacetamido]-γ-butyrolactone, aldimorph, anilazine, benalaxyl, benomyl, biloxazol, binapacryl, bitertanol, blasticidin S, bromuconazole, bupirimate, buthiobate, captafol, captan, carbendazim, carboxin, chlorbenzthiazone, chloroneb, chlorothalonil, chlorozolinate, copper containing compounds such as copper oxychloride, copper sulphate and Bordeaux mixture, cycloheximide, cymoxanil, cyproconazole, cyprofuram, di-2-pyridyl disulphide 1,1'-dioxide, dichlofluanid, dichlone, diclobutrazol, diclomezine, dicloran, difenoconazole, dimethamorph, dimethirimol, diniconazole, dinocap, ditalimfos, dithianon, dodemorph, dodine, edifenphos, etaconazole, ethirimol, ethyl (Z)-N-benzyl-N-([methyl(methylthioethylideneamino-oxycarbonyl)amino]thio)-ε-alaninate, etridiazole, fenapanil, fenarimol, fenfuram, fenpiclonil, fenpropidin, fenpropimorph, fentin acetate, fentin hydroxide, flutolanil, flutriafol, flusilazole, folpet, fosetyl-aluminium, fuberidazole, furalaxyl, furconazole-cis, guazatine, hexaconazole, hydroxyisoxazole, imazalil, imibenconazole, iprobenfos, iprodione, isoprothiolane, kasugamycin, mancozeb, maneb, mepanipyrim, mepronil, metalaxyl, methfuroxam, metsulfovax, myclobutanil, neoasozin, nickel dimethyldithiocarbamate, nitrothal-isopropyl, nuarimol, ofurace, organomercury compounds, oxadixyl, oxycarboxin, pefurazoate, penconazole, pencycuron, phenazin oxide, phthalide, polyoxin D, polyram, probenazole, prochloraz, procymidone, propamocarb, propiconazole, propineb, prothiocarb, pyrazophos, pyrifenox, pyroquilon, pyroxyfur, pyrrolnitrin, quinomethionate, quintozene, SSF-109, streptomycin, sulphur, tebuconazole, techlofthalam, tecnazene, tetraconazole, thiabendazole, thicyofen, thiophanate-methyl, thiram, tolclofos-methyl, triacetate salt of 1,1'-iminodi(octamethylene)diguanidine, triadimefon, triadimenol, triazbutyl, tricyclazole, tridemorph, triforine, validamycin A, vinclozolin, zarilamid and zineb. The compounds of general formula (I) can be mixed with soil, peat or other rooting media for the protection of plants against seed-borne, soil-borne or foliar fungal diseases.

Suitable insecticides which may be incorporated in the composition of the invention include buprofezin, carbaryl, carbofuran, carbosulfan, chlorpyrifos, cycloprothrin, demeton-s-methyl, diazinon, dimethoate, ethofenprox, fenitrothion, fenobucarb, fenthion, formothion, isoprocarb, isoxathion, monocrotophos, phenthoate, pirimicarb, propaphos and XMC.

Plant growth regulating compounds are compounds which control weeds or seedhead, formation, or selectively control the growth of less desirable plants (e.g. grasses).

Examples of suitable plant growth regulating compounds for use with the invention compounds are 3,6-dichloropicolinic acid, 1-(4-chlorophenyl)-4,6-dimethyl-2-oxo-1,2-dihydropyridine-3-carboxylic acid, methyl-3,6-dichloroanisate, abscisic acid, asulam, benzoylprop-ethyl, carbetamide, daminozide, difenzoquat, dikegulac, ethephon, fenpentezol, fluoridamid, glyphosate, glyphosine, hydroxybenzonitriles (e.g. bromoxynil), inabenfide, isopyrimol, long chain fatty alcohols and acids, maleic hydrazide, mefluidide, morphactins (e.g. chlorfluoroecol), paclobutrazol, phenoxyacetic acids (e.g. 2,4-D or MCPA), substituted benzoic acid (e.g. triiodobenzoic acid), substituted quaternary ammonium and phosphonium compounds (e.g. chloromequat, chlorphonium or mepiquatchloride), tecnazene, the auxins (e.g. indoleacetic acid, indolebutyric acid, naphthylacetic acid or naphthoxyacetic acid), the cytokinins (e.g. benzimidazole, benzyladenine, benzylaminopurine, diphenylurea or kinetin), the gibberellins (e.g. $GA_3$, $GA_4$ or $GA_7$) and triapenthenol.

The following Examples illustrate the invention.

Where shown, infrared and NMR data are selective; no attempt is made to list every absorption in all cases. The following abbreviations are used throughout:

| DMF = N,N-dimethylformamide | s = singlet |
|---|---|
| THF = tetrahydrofuran | t = triplet |
| d = doublet | m = multiplet |
| q = quintuplet | NMR = nuclear magnetic resonance |
| b = broad | |
| IR = infrared | mp = melting point |

EXAMPLE 1

This example illustrates the preparation of N,N-dimethyl-3-chloro-5-(2'-fluoro-2'-methylpropionamido)-pyridine-2-carboxamide (Compound No. 7 of Table I).

Step 1

The preparation of ethyl α-ethoxycarbonyl-3-chloro-5-nitropyridine-2-acetate.

Diethylmalonate (5.41 g) was added dropwise to sodium hydride (1.84 g of a 55% dispersion in oil) stirred in dry THF (50 ml) at room temperature under nitrogen. After completion of the addition the mixture was refluxed for 1 hour, and then 2,3-dichloro-5-nitropyridine (5.02 g) in dry THF (20 ml) was added dropwise, the reaction changing colour from green to red. The mixture was refluxed for 4 hours and then stood overnight. Further sodium hydride (0.537 g of a 55% dispersion in oil) was then added, and the reaction stirred at room temperature for 3 hours. The mixture was then poured into water, extracted with ether, and the ether extract dried over magnesium sulphate and evaporated to give the desired product as an oil which crystallised on standing (4.15 g); $^1$HNMR ($CDCl_3$, 270 Mhz) δ: 1.30(6H,t), 4.31(4H,q), 5.28(1H,s), 8.53(1H,d), 9.30(1H,d) ppm.

Step 2

The preparation of 3-chloro-2-methyl-5-nitropyridine.

Ethyl α-ethoxycarbonyl-3-chloro-5-nitropyridine-2-acetate (3.56 g) was heated in concentrated sulphuric acid (70 ml) and water (35 ml) at 180° C. for 4 hours. After cooling, the mixture was poured into ice and water, and extracted with ethyl acetate. The organic layer was washed with water, dried over magnesium sulphate and evaporated to yield the desired product as a red-brown liquid (1.40 g); $^1$HNMR ($CDCl_3$, 270 Mhz) δ: 2.78(3H,s), 8.45(1H,d), 9.22(1H,s) ppm.

Step 3

The preparation of 3-chloro-5-nitropyridine-2-carboxaldehyde.

3-chloro-2-methyl-5-nitropyridine (1.109 g) was refluxed with selenium dioxide (0.909 g) in dry 1,4-dioxan (35 ml) under nitrogen, for 30 hours. The reaction mixture was then cooled to room temperature, filtered through celite, poured into water and extracted with ethyl acetate. The organic layer was dried over magnesium sulphate and evaporated to give a reddish-brown liquid which consisted of a mixture containing 85% of the desired aldehyde and 15% of the starting material, which was used without purification; $^1$HNMR (CDCl$_3$,270 Mhz) δ: 8.65(1H,d), 9.49(1H,d), 10.34(1H,s) ppm.

Step 4

The preparation of 3-chloro-5-nitropyridine-2-carboxylic acid.

Crude 3-chloro-5-nitropyridine-2-carboxaldehyde (1.6 g containing approximately 1.0 g of the aldehyde) was stirred at 10° C. in a mixture of acetonitrile (35 ml) and water (3 ml) containing sodium dihydrogen orthophosphate (0.201 g) and hydrogen peroxide (0.80 g of a 28% aqueous solution). Sodium chlorite (1.21 g of 80% material) in water (13 ml) was added dropwise, and after the completion of the addition the reaction was stirred for 1.5 hours at 10° C. Then further sodium hydrogen orthophosphate (0.107 g), hydrogen peroxide (0.407 g of a 28% solution) and sodium chlorite (0.499 g) were added, and the reaction stirred for 2 hours. Sodium metabisulphite was added to destroy excess hydrogen peroxide and sodium chlorite, and the mixture extracted with ethyl acetate. The organic layer was extracted with aqueous sodium bicarbonate, and the aqueous solution acidified with dilute hydrochloric acid, and extracted with ethyl acetate. This ethyl acetate solution was dried and evaporated to give the desired acid as a pale brown solid (0.829 g), containing about 10% of the starting aldehyde. It was used without purification; $^1$HNMR (CDCl$_3$,270 MHz) δ: 8.30(1H,d), 8.45(1H,d) ppm; IR (nujol) ν: 2500 (b), 1725 cm$^{-1}$.

Step 5

The preparation of N,N-dimethyl-3-chloro-5-nitropyridine-2-pyridinecarboxamide.

Oxalyl chloride (0.548 g) in dry methylene chloride (5 ml) was added dropwise to a stirred solution of the crude 3-chloro-5-nitropyridine-2-carboxylic acid (0.792 g of material 90% pure) in dry methylene chloride (60 ml) and a drop of DMF was added. After stirring for 2 hours, a saturated solution of dimethylamine in methylene chloride (10 ml; prepared by bubbling dimethylamine gas into the solvent for 20 minutes) was added over 30 minutes, keeping the temperature at 0°-5° C. After stirring for 1.5 hours at 0°-10° C. the solution was washed with dilute hydrochloric acid and then dilute aqueous sodium hydroxide and was then dried over magnesium sulphate to give the desired product as an orange crystalline solid, (0.775 g); $^1$HNMR (CDCl$_3$, 270 Mhz) δ: 2.89(3H,s), 3.20(3H,s), 8.59(1H,d), 9.35(1H,d) ppm; IR (nujol) ν: 3110, 3070, 1655 cm$^{-1}$.

Step 6

The preparation of N,N-dimethyl-3-chloro-5-aminopyridine-2-carboxamide.

Stannous chloride (5.795 g) in concentrated hydrochloric acid (10 ml) was added to N,N-dimethyl-3-chloro-5-nitropyridine-2-carboxamide (0.684 g) in concentrated hydrochloric acid (10 ml), and the mixture stirred at 10°-15° C. for 0.5 hour. The mixture was then basified with aqueous sodium hydroxide, and extracted with methylene chloride, which was dried over magnesium sulphate and evaporated to give the desired product as a white solid (0.514 g); $^1$HNMR(CDCl$_3$,270 Mhz) δ: 2.89(3H,s), 3.11(3H,s), 3.97(2H,bs), 6.99(1H,d), 7.91(1H,d) ppm; IR (nujol) ν: 3400, 3200, 1650-30 cm$^{-1}$.

Step 7

The preparation of N,N-dimethyl-3-chloro-5-(2'-fluoro-2-methylpropionamido)pyridine-2-carboxamide.

Oxalyl chloride (0.412) in dry methylene chloride (5 ml was added dropwise to 2-fluoroisobutyric acid (0.315 g; prepared as described in co-pending application No. Z828) in dry methylene chloride (10 ml) containing a trace of DMF, and the mixture stirred for 3 hours at room temperature. This solution was then added dropwise to a solution of N,N-dimethyl-3-chloro-5-aminopyridine-2-carboxamide (0.489 gm) in dry methylene choloride (100 ml) containing triethylamine (0.517 gm), at 0°-5° C. The reaction was then stirred for 2 hours, and was then washed with dilute hydrochloric acid and then sodium hydroxide. The methylene chloride layer was dried over magnesium sulphate, and evaporated to give an orange solid (0.270 gm), which was triturated with hexane to give the desired compound as an orange-brown solid (0.018 gm), mp 159°-162° C.; $^1$HNMR (CDCl$_3$,270Mhz) δ: 1.69(6H,d), 2.86(3H,s), 3.16(3H,s), 8.31(1H,d), 8.41(1H,d), 8.51(1H,d) ppm.

The following are examples of compositions suitable for agricultural and horticultural purposes which can be formulated from the compounds of the invention. Such compositions form another aspect of the invention. Percentages are by weight.

EXAMPLE 2

An emulsifiable concentrate is made up by mixing and stirring the ingredients until all are dissolved.

| | |
|---|---|
| Compound No. 1 of Table I | 10% |
| Benzyl alcohol | 30% |
| Calcium dodecylbenzenesulphonate | 5% |
| Nonylphenolethoxylate (13 mole ethylene oxide) | 10% |
| Alkyl benzenes | 45% |

EXAMPLE 3

The active ingredient is dissolved in methylene dichloride and the resultant liquid sprayed on to the granules of attapulgite clay. The solvent is then allowed to evaporate to produce a granular composition.

| | |
|---|---|
| Compound No. 1 of Table I | 5% |
| Attapulgite granules | 95% |

EXAMPLE 4

A composition suitable for use as a seed dressing is prepared by grinding and mixing the three ingredients.

| | |
|---|---|
| Compound No. I of Table I | 50% |
| Mineral oil | 2% |
| China clay | 48% |

EXAMPLE 5

A dustable powder is prepared by grinding and mixing the active ingredient with talc.

| Compound No. 1 of Table I | 5% |
|---|---|
| Talc | 95% |

EXAMPLE 6

A suspension concentrate is prepared by ball milling the ingredients to form an aqueous suspension of the ground mixture with water.

| Compound No. 1 of Table I | 40% |
|---|---|
| Sodium lignosulphonate | 10% |
| Bentonite clay | 1% |
| Water | 49% |

This formulation can be used as a spray by diluting into water or applied directly to seed.

EXAMPLE 7

A wettable powder formulation is made by mixing together and grinding the ingredients until all are thoroughly mixed.

| Compound No. I of Table I | 25% |
|---|---|
| Sodium lauryl sulphate | 2% |
| Sodium lignosulphonate | 5% |
| Silica | 25% |
| China clay | 43% |

EXAMPLE 8

The compounds were tested against a variety of foliar fungal diseases of plants. The technique employed was as follows.

The plants were grown in John Innes Potting Compost (No. 1 or 2) in 4 cm diameter minipots. The test compounds were formulated either by bead milling with aqueous Dispersol T or as a solution in acetone or acetone/ethanol which was diluted to the required concentration immediately before use. For the foliage diseases, the formulations (100 ppm active ingredient) were sprayed onto the foliage and applied to the roots of the plants in the soil. The sprays were applied to maximum retention and the root drenches to a final concentration equivalent to approximately 40 ppm a.i. in dry soil. Tween 20, to give a final concentration of 0.05%, was added when the sprays were applied to cereals.

For most of the tests the compound was applied to the soil (roots) and to the foliage (by spraying) one or two days before the plant was inoculated with the disease. An exception was the test on *Erysiphe graminis* in which the plants were inoculated 24 hours before treatment. Foliar pathogens were applied by spray as spore suspensions onto the leaves of test plants. After inoculation, the plants were put into an appropriate environment to allow infection to proceed and then incubated until the disease was ready for assessment. The period between inoculation and assessment varied from four to fourteen days according to the disease and environment.

The disease control was recorded by the following grading:
4 = no disease
3 = trace-5% of disease on untreated plants
2 = 6-25% of disease on untreated plants
1 = 26-59% of disease on untreated plants
0 = 60-100% of disease untreated plants The results are shown in Table II.

TABLE II

| Compound No. | *Puccinia recondita* (Wheat) | *Erysiphe graminis* (Wheat) | *Venturia inaequalis* (Apples) | *Plasmopara viticola* (Vines) | *Phytophthora infestans* (Tomatoes) |
|---|---|---|---|---|---|
| 7 | — | — | — | $4^a$ | $3^a$ |
| 9 | 0 | 0 | 0 | 4 | 3 |
| 11 | — | — | — | $4^a$ | $2^b$ |
| 24 | 0 | 0 | 0 | 4 | 3 |

$^a$root drench application only @ 100 ppm.
$^b$root drench application only @ 50 ppm.
— no result.

TABLE I $$R^4-\overset{O}{\underset{\|}{C}}-\underset{H}{\underset{|}{N}}\underset{}{\overset{A}{\diagup}}\overset{}{\underset{N}{\diagdown}}\overset{O}{\underset{\|}{C}}-\underset{R^2}{\underset{|}{N}}-R^1 \quad (II)$$

*$R^2$ of Compound No. 32 is 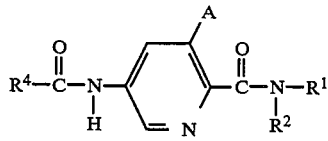—CH$_2$

*$R^2$ of Compound No. 33 is 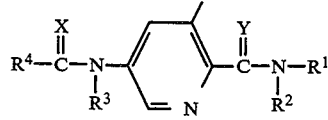—

CHEMICAL FORMULAE
(in description)

$$R^4-\overset{X}{\underset{\|}{C}}-\underset{R^3}{\underset{|}{N}}\underset{}{\overset{A}{\diagup}}\overset{}{\underset{N}{\diagdown}}\overset{Y}{\underset{\|}{C}}-\underset{R^2}{\underset{|}{N}}-R^1 \quad (I)$$

Scheme 1

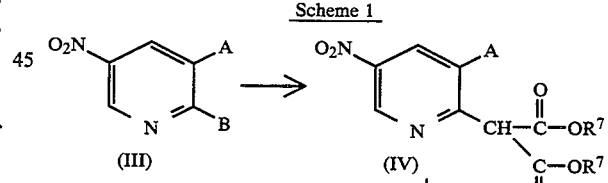

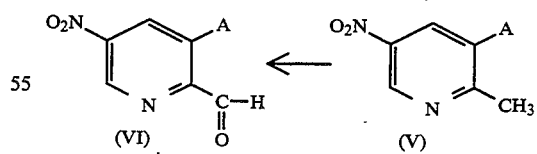

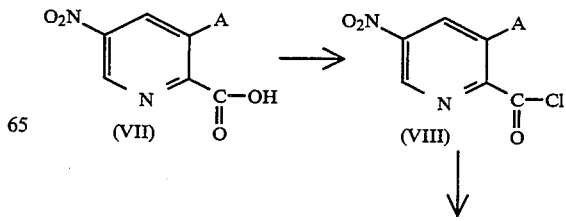

-continued
Scheme 1

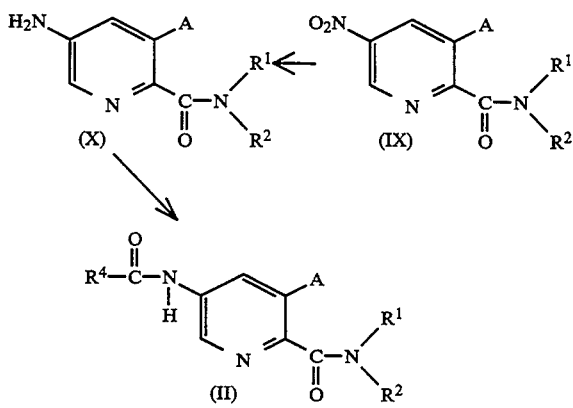

We claim:
1. A compound of the formula (I)

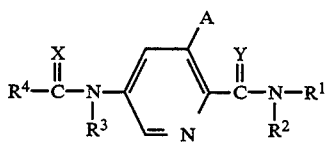

A is fluoro, chloro, bromo, iodo, $C_{1-4}$ alkyl, $C_{1-4}$ alkoxy, halo($C_{1-4}$)alkyl, $C_{1-4}$ alkoxylmethyl, $C_{1-4}$ alkylthiomethyl, $C_{2-4}$ alkenyl, $C_{2-4}$ alkynyl, $C_{1-4}$ alkoxycarbonyl, $C_{1-4}$ alkylcarbonyl, formyl, cyano, nitro or $C_{1-4}$ alkylthio; $R^1$ and $R^2$ are independently $C_{1-4}$ alkyl, $C_{3-6}$ alkenyl optionally substituted with halogen, $C_{3-6}$ alkynl optionally substituted with halogen $C_{1-4}$ alkoxy, halo($C_{1-4}$)alkyl, $C_{3-6}$ cycloalkyl, $C_{3-6}$ cycloalkyl($C_{1-4}$)alkyl, $C_{1-4}$ alkoxy($C_{1-4}$)alkyl, $C_{1-4}$ alkylthio($C_{1-4}$)alkyl or cyano; $R^3$ is H; $R^4$ is $C_{2-8}$ alkyl, $C_{2-8}$ alkenyl, $C_{2-8}$ alkynyl, or $C_{3-6}$ cycloalkyl, all of which may be optionally substituted with halogen, $C_{1-4}$ alkyl, $C_{1-4}$ alkoxy, $C_{1-4}$ alkylthio, cyano, $C_{1-4}$ alkylcarbonyl, $C_{1-4}$ alkoxycarbonyl, azido, nitro, isocyano or $NR^5R^6$ where $R^5$ and $R^6$ are independently H, $C_{1-4}$ alkyl, $C_{1-4}$ alkylcarbonyl, or formyl; and X and Y are independently oxygen or sulphur.

2. A compound according to claim 1 in which $R^4$ is $R(CH_3)_2C-$ wherein R is halogen, $C_{1-4}$ alkyl or $C_{1-4}$ alkoxy.

3. A compound according to claim 1 in which A is chloro, bromo, fluoro or $C_{1-4}$ alkyl; $R^1$ and $R^2$ are $C_{1-4}$ alkyl; $R^3$ is H; $R^4$ is $C_{2-8}$ alkyl optionally substituted with halogen or $C_{1-4}$ alkoxy; and X and Y are both oxygen.

4. A fungicidal composition comprising a fungicidally effective amount of a compound according to claim 1 and a fungicidally acceptable carrier or diluent therefor.

5. A method of combating fungi which comprises applying to a plant, to a seed of a plant or to the locus of the plant or seed a fungicidally effective amount of a compound according to claim 1 or a composition according to claim 4.

6. A compound of the formula (II)

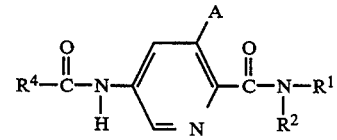

wherein $R^1$ and $R^2$ are independently $C_1-C_4$ alkyl, $C_3-C_6$ alkenyl, $C_3-C_6$ alkynyl, $C_1-C_4$ alkoxy or halo($C_1-C_4$)alkyl; and $R^4$ is $C_1-C_6$ alkyl, halo($C_3-C_6$)alkyl, and alkoxyalkyl, and A is halo, $C_1-C_4$ alkyl, $C_1-C_4$ alkoxy, halo($C_1-C_4$)alkyl, $C_2-C_4$ alkenyl, $C_2-C_4$ alkynyl, $C_1-C_4$ alkylthio, nitro, cyano, formyl, $C_1-C_4$ alkoxycarbonyl and $C_1-C_4$ alkylcarbonyl.

7. A compound according to claim 6 in which $R^1$ and $R^2$ are $C_1-C_4$ alkyl; $R^4$ is alkyl or haloalkyl; and A is halo, methyl, ethyl, methoxy and haloalkyl.

8. A fungicidal composition comprising a fungicidally effective amount of a compound according to claim 6 and a fungicidally acceptable carrier or diluent therefor.

9. A composition according to claim 8 in which A is halo, $R^1$ and $R^2$ are independently methyl or ethyl and $R^4$ is t-butyl or $F(CH_3)_2C$.

10. A method of combating fungi which comprises applying to a plant, to a seed of a plant or to the locus of a plant or seed a fungicidally effective amount of a compound according to claim 6.

* * * * *